July 29, 1958 E. V. GOLDSMITH ET AL Plant Pat. 1,736
VARIETY OF STRAWBERRY
Filed June 29, 1956
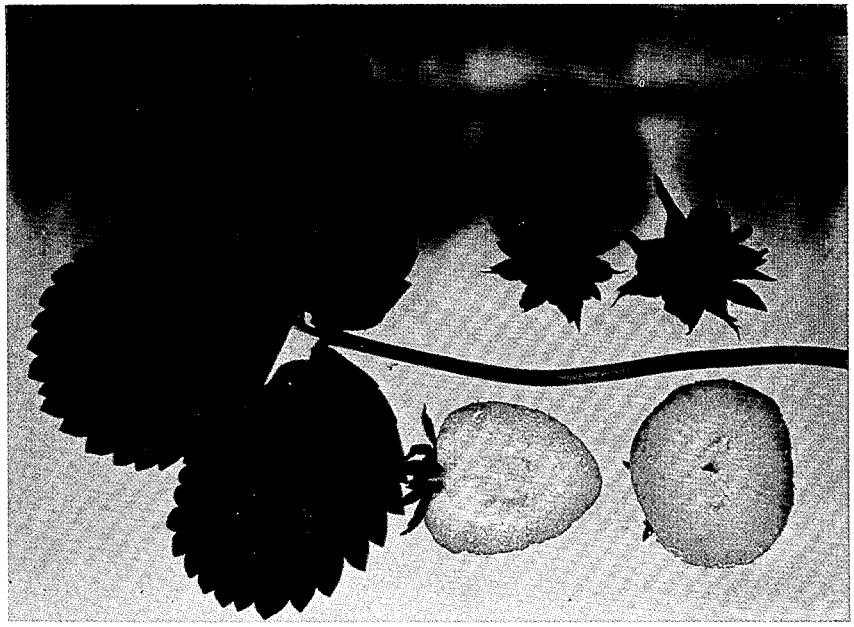
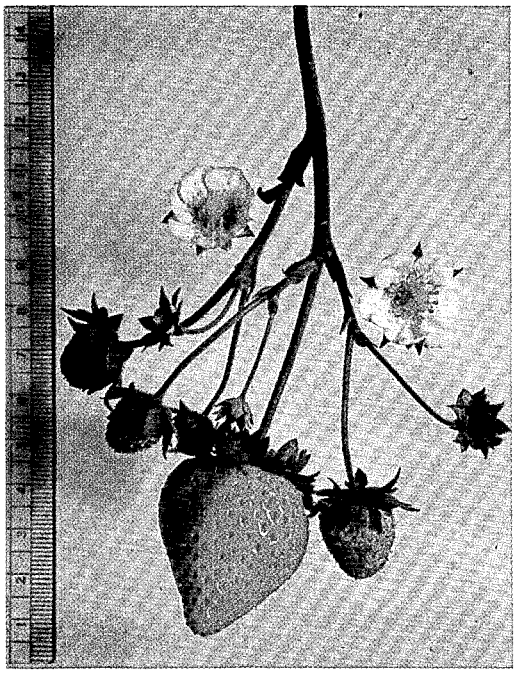
INVENTORS
HAROLD E. THOMAS and
MARGARET S. GOLDSMITH
EXECUTRIX FOR THE ESTATE OF
EARL V. GOLDSMITH
BY Hansen and Lane
THEIR ATTORNEYS United States Patent Office Plant Pat. 1,736

Patented July 29, 1958

1,736

VARIETY OF STRAWBERRY

Earl V. Goldsmith, deceased, late of Morgan Hill, Calif., by Margaret S. Goldsmith, executrix, San Jose, and Harold E. Thomas, Morgan Hill, Calif.; said Margaret S. Goldsmith assignor to The Strawberry Institute of California Application June 29, 1956, Serial No. 595,039

1 Claim. (Cl. 47—62)

This invention relates to a distinctly new strawberry variety resulting from a cross of two University of California seedling selections numbered 800.13 and 814.6. The seedlings resulting from this cross were first fruited at Waterford, California, and the plant embodying the present invention was selected from this group of seedlings. Asexual reproduction was carried out in the same area by rooting runner plants which originated from the mother seedling. Further testing was carried on in various parts of California during the intervening seasons. As a result of these tests the selected plants have shown merit in numerous locations on properties of members of The Strawberry Institute of California.

In the accompanying drawings two photographic pictures are presented:

The uppermost picture shows a view of one leaf of the plant showing the color and characteristics thereof; a top plan view of the calyx bud of the fruit; a fruit side view of the calyx from which the fruit has been removed; a transverse section through the fruit; and a longitudinal section through the fruit and calyx.

The lowermost picture shows a side view of an inflorescence or blossom and also a fruit bearing stem.

The plant of the present invention is a vigorous growing, medium dense to semi-open type with many medium sized leaves. The leaves have a dark vivid green color, but are not glossy. Some fine wrinkling occurs between the veins, but never as wrinkly or as coarse as are the leaves in the Shasta variety. The Shasta is a variety introduced in 1945 by applicants herein for the University of California. The Shasta is a standard variety grown in California more than in any other State. The Shasta variety although not patented is known to the Bureau of Plant Industry, Agricultural Research Center at Beltsville, Maryland. The plant of the present application is generally not as open as in the Shasta variety and has more leaves. The strongest character of the plant of this invention is its ruggedness; its comparative tolerance to virus diseases prevailing in California; and its ability to grow well under poor soil conditions.

Most of the fruit of the present plant are borne on an inflorescence somewhat like that of the Shasta variety in that the secondary fruiting stems, or the peduncle which holds the secondary fruit, branch from two axils on the main fruiting stem with the pedicel of the primary berries originating from one of the axils. The berries of this new plant are glossy and bright and are round conic to long conic in form. They are generally glossier, and slightly larger and more symmetrical than the fruit of the Shasta variety. The medium sized seeds on the berries of the present plant are held below to even with the surface as distinguished from the exerted seeds in the Shasta variety. The calyx of the fruit in the new plant is similar to that of the Shasta in that it is large and has serrated sepals which overlap making two rows. The hair on the pedicel of the present plant is perpendicular to the pedicel while on Shasta the angle is between 10 to 45 degrees with many of the hairs held in an irregular way.

Pickers harvesting the berry of the present plant for processing have trouble stemming the fruit in that the sepals of the calyx often come off leaving the small stem attached to the berry. Despite the difficulty in stemming and the stringy nature of the core, the berries of the present plant are considered satisfactory for freezing. The flesh of the berry in this new plant is light in color during the last of the picking season, but not objectionably so. The ability of this new variety to produce large glossy fruit and a large crop even when exposed to virus and adverse soil conditions makes it a good commercial berry. The virus tolerance of this new variety was discovered when its plants were grown by way of comparison in the same area with the Shasta variety. The test plots were in the San Martin and Watsonville areas of California where virus diseases are known to be prevalent and most severe to strawberries. The present variety maintained its vigor for a period of 1 to 2 years longer than did the Shasta plant which appears to be the result of a resistance to the virus diseases present and prevailing in that area.

The fruiting season for this variety is normally about the same as that of the Shasta variety. It usually starts during the middle or last of April in the interior and warmer coastal valleys of California and tends to yield a three crop type of production continuing until cold weather or fall rains occur. In southern California production starts earlier, and in cool coastal areas somewhat later.

In comparison to the berries of the Shasta variety, the dessert quality of the berries of the new plant are about the same, with a mild sub-acid flavor; it has no particular aroma; and during the last of the season the flesh may be slightly stringy.

This new variety of plane is susceptible to Verticillium wilt and the red stele disease. It is affected by mildew, on the fruit and foliage. It is slightly tolerant to two spotted mite and cyclamen mite.

The detailed varietal characteristics described below were observed in second year test fruiting beds, during August, September, and October at Watsonville, California, which is a cool coastal area near the Pacific Ocean. The color terminology is in accordance with Ridgeways Color Standards and Nomenclature (1912 edition).

Plant: Medium large, vigorous, semi-open to medium dense, with a vigorous root system and good longevity.

Leaves: Numerous; petiole medium long, mostly 15 to 25 cm., petiolule of central leaflet mostly 5 to 7 mm. Color—upperside—Dusky Olive Green, Plate XLI; size, mostly 4 to 8 cm. with an average of 7 cm. The vein on the upperside of the central leaflet at the end of the petiolule and extending outward 10 mm. is not noticeably wide, usually less than 1 mm. The leaflet surface is bright green, but not shiny; some wrinkle occurs between the veins. The outline of the serrations on the margin of the leaflets is ovate with an acute apex. Color—upperside—Dusky Olive Green, Plate XLI; lowerside—Bryce Green XVII.

Runners: Vigorous, medium to long internodes, producing many runners the first year and a few the second in fruiting beds.

Inflorescence: Medium long, mostly 20 to 30 cm.; some bloom is visible above plant. On most inflorescences the peduncles which hold the secondary berries branch from two axils on the main fruiting stem and the pedicel holding the primary berry originates from one of the axils. The internode length between the axils varies between 5 and 50 mm. The hair on the tertiary pedicels 20 mm. from the flowers is perpendicular to the pedicels.

Fruit: Medium large to large, 40 to 45 mm. in length, and 35 to 40 mm. in width (size of primaries or well developed secondaries), round conic to long conic in form with some wedge shaped berries in the spring. Many berries have a characteristic pointed to slightly pinched apex caused by the failure of a few seeds to fertilize, usually 10 to 15 mm. below the apex. This gives a slightly concave or depressed area on the side of the fruit. This abnormality does not detract from the good appearance of the fruit. The shoulders are large and rounded giving an outline like the upper half of a heart. The surface has a bright high gloss. During the last of the picking season the shoulders take on a whitish pink to a pink color. Color—Carmine Red, Plate I. Flesh—may become light in color and slightly stringy especially during the last of the season; color—Rose Doree, Plate IV. Core—solid but may be stringy during some crops. Seeds—medium in size, held below to even with the surface; color—Apricot Yellow, Plate IV.

Calyx: Mostly large with diameter 30 to 40 mm. averaging 35 mm. Sepals—12 to 16 in number with two rows which overlap. The row adjoining the fruit has broad sepals while those on the other row are narrower. The sepals have an apex which is usually serrated. Most of the calyxes are clasping but a few tend to be reflexed. Color—upperside (side next to the fruit)—Deep Dull Yellow Green, Plate XXXII; lowerside—Cress Green, Plate XXXI.

We claim:

A new and distinct variety of strawberry plant, substantially as herein shown and described, characterized by its rugged plant which is tolerant of the virus diseases; and by its high production, its bright, glossy, round conic to long conic fruit which carries well on the market.

No references cited.